US006465245B1

(12) United States Patent
Walton et al.

(10) Patent No.: US 6,465,245 B1
(45) Date of Patent: Oct. 15, 2002

(54) PROCESSOR DEVICE WITH FUME EXTRACTION

(76) Inventors: George Alan Walton, 9 Oakdene Way, Tarporley, Cheshire (GB); Susan Jane Graham, 19 Grasmere Road, Frodsham, Cheshire (GB)

( * ) Notice: Subject to any disclaimer, the term of this patent is extended or adjusted under 35 U.S.C. 154(b) by 0 days.

(21) Appl. No.: 09/962,174

(22) Filed: Sep. 24, 2001

(30) Foreign Application Priority Data

Jul. 23, 2001 (GB) .............................................. 0117919

(51) Int. Cl.[7] .............................................. C12M 1/00

(52) U.S. Cl. ............................... 435/307.1; 435/283.1; 422/102; 220/227; 220/810; 220/811; 220/913; 220/DIG. 27

(58) Field of Search .......................... 422/99, 101, 102, 422/104; 220/227, 810, 811, 913, DIG. 27; 435/283.1, 307.1

(56) References Cited

U.S. PATENT DOCUMENTS 5,424,040 A * 6/1995 Bjornsson .................. 422/101

* cited by examiner

*Primary Examiner*—David A. Redding

(74) *Attorney, Agent, or Firm*—Fulwider Patton Lee & Utecht, LLP

(57) ABSTRACT

A laboratory apparatus, such as a tissue processor, includes a container for containing material which may emit noxious fumes, the container having a closure moveable between an open position and a closed position in which it closes off or opens a mouth of the container. A fume collecting arrangement is provided including vents provided adjacent the mouth or opening of the container and apparatus operable to draw in air, with fumes escaping from the container, whilst the closure is in the open position, and to pass the air carrying the fumes for treatment or to a disposal outlet. The apparatus operable to draw in air may be electrically operated and may be controlled by a switch operated automatically by opening and closing said closure.

7 Claims, 3 Drawing Sheets

PROCESSOR DEVICE WITH FUME EXTRACTION

BACKGROUND OF THE INVENTION

THIS INVENTION relates to devices, primarily laboratory apparatus, such as tissue processors for processing biological tissue, which comprise containers to which occasional access is required and which may contain material likely to emit noxious fumes. The invention is of particular, but not exclusive, utility in relation to tissue processors for processing specimens of biological tissue, for example for mounting on microscope slides. Such a tissue processor has a reaction chamber containing reagents which may release hazardous fumes when the lid is opened to add specimens. The most critical processing fluid in common use in this context is formalin. In the past, it has been common merely to allow such fumes to escape into the surrounding atmosphere when the processor lid is opened, on the basis that the duration of exposure to the fumes should be too short to present any significant health hazard to personnel. However, such an approach is becoming less acceptable and it is becoming more common to install separate fume containers and extraction enclosures around such tissue processors.

SUMMARY OF THE INVENTION

It is an object of the invention to provide a laboratory apparatus for use with material liable to emit noxious fumes and which is capable of minimizing the escape of such fumes into the laboratory environment without the inconvenience and obstruction caused by a secondary enclosure.

In accordance with the present invention, there is provided a laboratory apparatus, such as a tissue processor, comprising a container for containing material which may emit noxious fumes, the container having a closure moveable between an open position and a closed position in which it closes off or opens a mouth of the container and wherein a fume collecting arrangement is provided comprising vents provided adjacent said mouth or opening of the container and means operable to draw in air, with fumes escaping from the container, whilst the closure is in said open position, and to pass the air carrying said fumes to treatment means or to a disposal outlet.

BRIEF DESCRIPTION OF THE DRAWINGS

An embodiment of the invention is described below by way of example with reference to the accompanying drawings in which.

DETAILED DESCRIPTION

Figure 1:
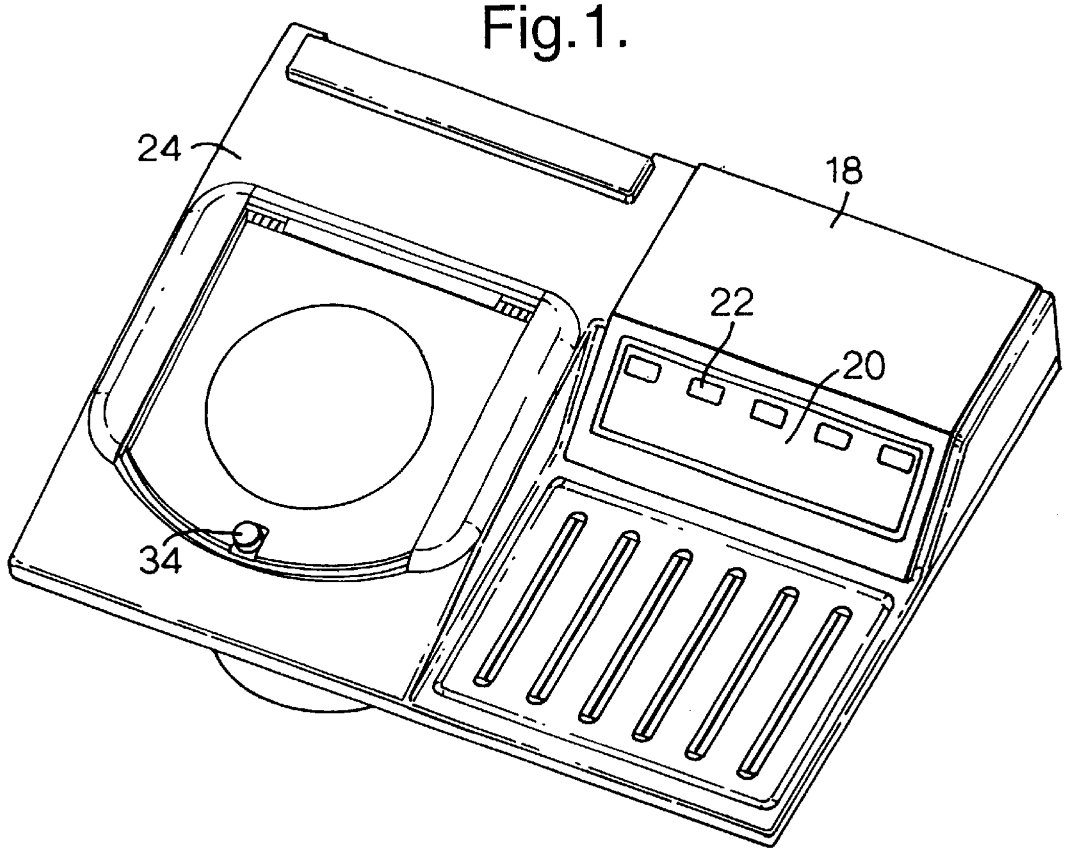
FIG. 1 is a perspective view from above of part of a tissue processor embodying the invention, with a lid thereof closed.
Figure 2:
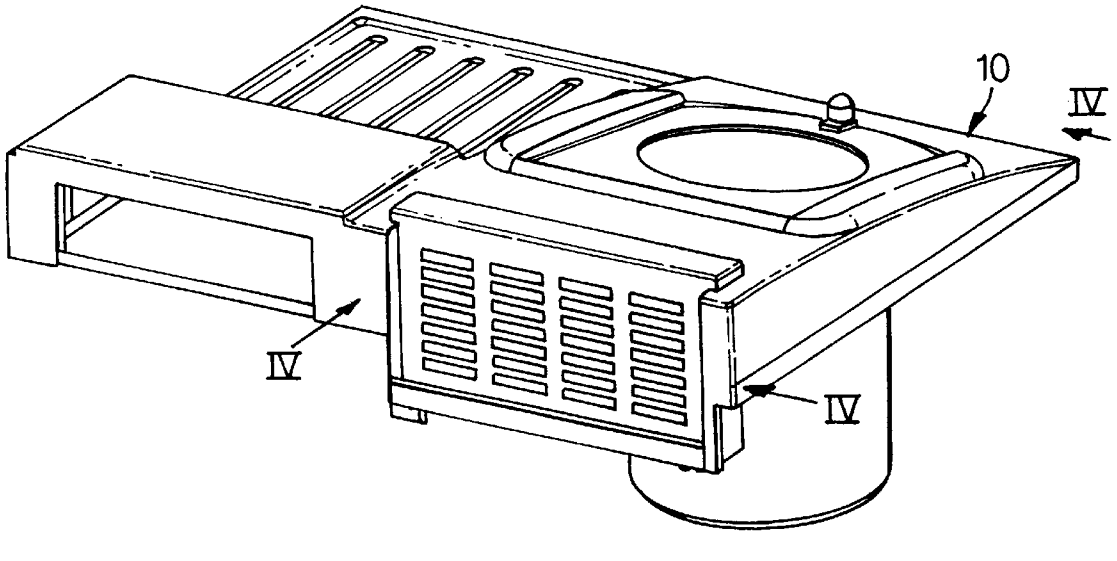
FIG. 2 is a rear perspective view of the part of FIG. 1.
Figure 5:
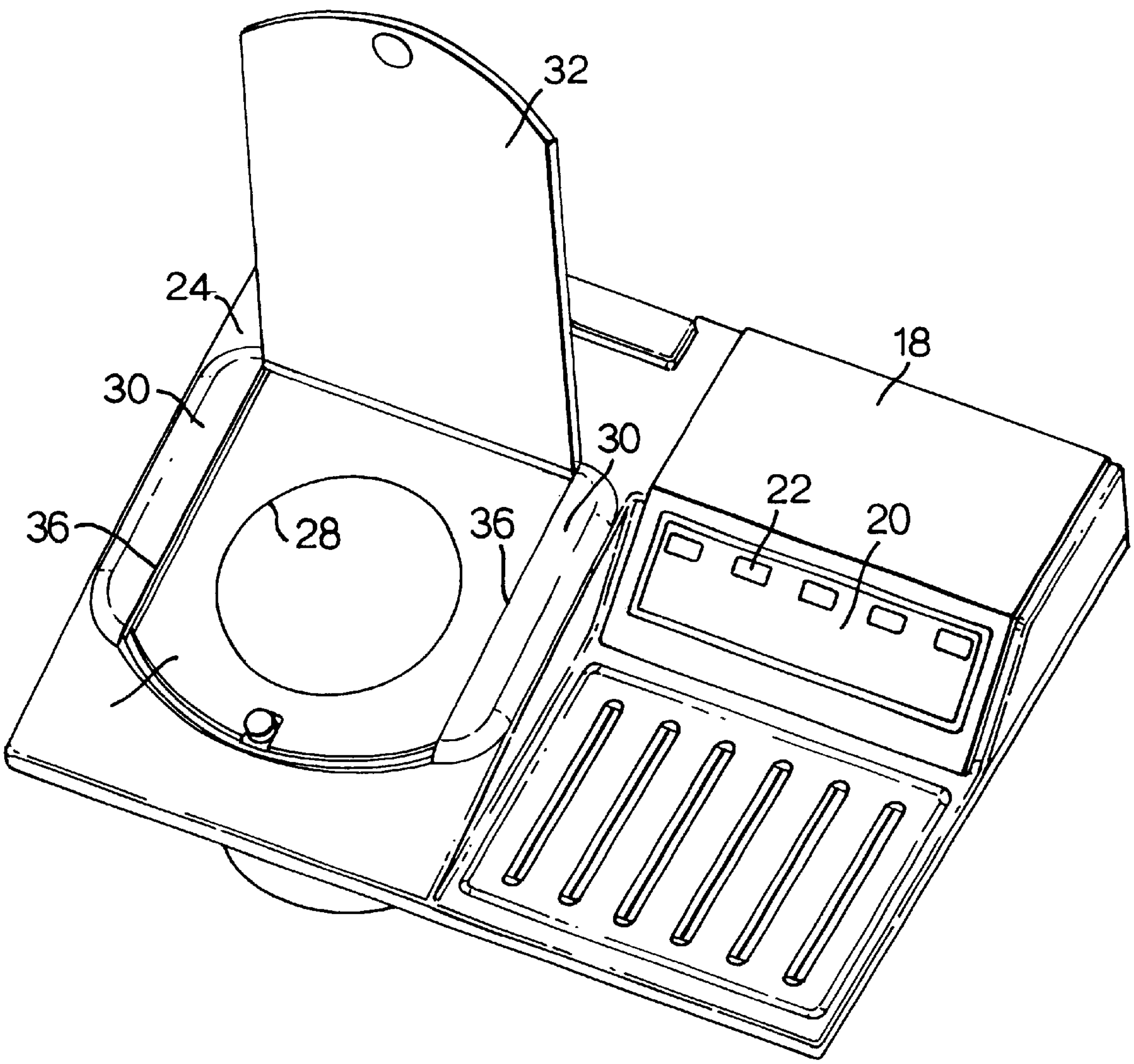
FIG. 5 is a view similar to FIG. 1 but showing the lid in the open position.

Referring to the drawings, the structure illustrated forms the upper part of a complete tissue processor unit of which the lower part (not shown) may be generally rectangular and may have vertical front, back and side walls and a supporting base, the upper part being secured to said lower part, for example by screws. Thus, the tissue processor shown comprises a panel 10 having lower peripheral edges 12, 13, 14 for engagement with opposing upper edges of said front and side walls of said lower part (not shown) of the tissue processor (not shown). On its upper side, the panel 10 provides a deck affording, on its right-hand side as viewed in FIGS. 1 and 5, towards the front of the deck, a generally horizontal surface which may be provided with recesses to receive specimen holders or the like and which, towards the rear, is provided with a raised housing 18 to receive control circuitry (not shown) and which housing 18 may provide, at its front, a control panel 20 with control buttons 22. To the left, as viewed in FIG. 1, of the unit, the panel 10 provides a portion 24 of the deck which may, as illustrated, slope upwardly from front to rear slightly. The apparatus includes a reaction chamber or vessel 26, located on the left side of the panel 10 as viewed in FIGS. 1 and 5, in the arrangement shown, and which is generally cylindrical, having its peripheral cylindrical wall centered on a vertical axis and terminating, at its upper end, on the interior of said cylindrical wall, in an opening 28 in a generally flat part 25 of the deck bounded on either side by a respective rib 30 projecting upwardly from the surrounding portions of the deck, so that, relative to the upper surfaces of the ribs 30, the flat part 25 is recessed somewhat. A lid 32 (see FIG. 5) is pivotally mounted between the ribs or shoulders 30. The lid 32 has a generally straight back edge, two parallel side edges perpendicular to the back edge and an arcuate front edge. In the closed position of the lid, as shown in FIG. 1, the slide edges of the lid lie close to respective opposing parallel slide faces of the ribs 30, whilst the rear edge of the lid lies adjacent the rear ends of the ribs 30. The lid 32 has a curved/arcuate front edge which forms a continuation of arcuate front edges of the ribs 30. In the closed position of the lid, the upper surface of the latter may be substantially flush with the upper surfaces of the ribs 30. The lid 32 may be moved from the closed position shown in FIG. 1 to the open or raised position shown in FIG. 5, by lifting the lid by means of an operating knob 34 and swinging the lid about its hinge to the open position shown in FIG. 5.

Figure 3:
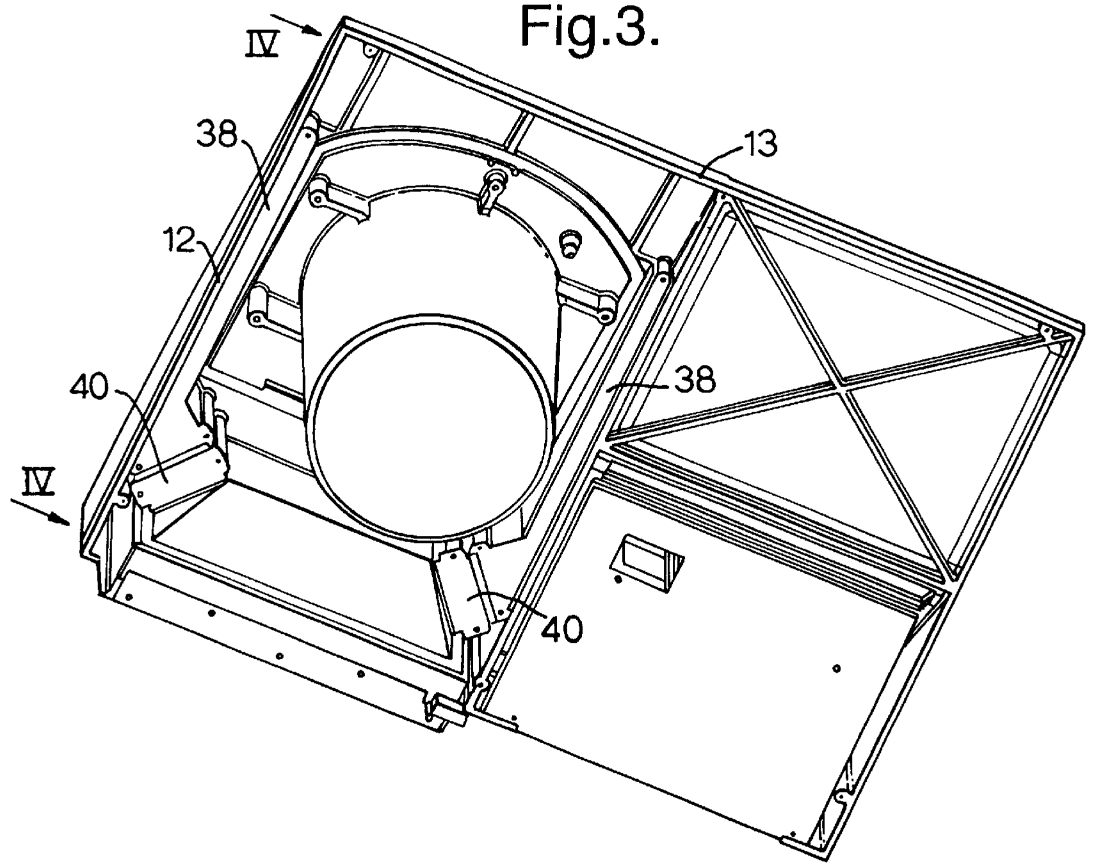
FIG. 3 is an underneath perspective view of the part of FIGS. 1 and 2.
Figure 4:
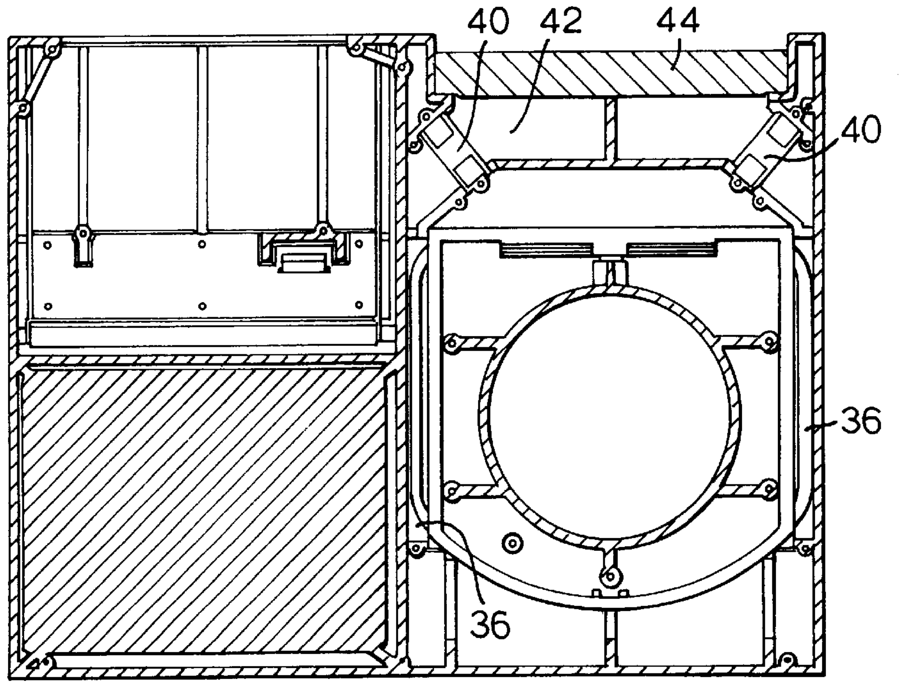
FIG. 4 is a view from below of the part of FIGS. 1 to 3, in sections substantially along the lines IV—IV indicated in FIGS. 2 and 3.

Provided along the lower edges of the opposing side walls of the ribs 30 or along the edges of the surface 25 adjoining these opposing side faces, are respective longitudinal slits or vents, indicated generally at 36 (see also FIG. 4), these slots opening into respective manifolds or ducts 38 on the underside of the panel 10. These ducts lead, via respective extraction fans 40 (FIGS. 3 and 4), driven by electric motors, (not shown), to an outlet chamber 42, from whence the air drawn in through the vents 36 by the fans 40 can pass through a filter 44 back into the laboratory space, or, if preferred, via appropriate ducting (not shown) to a more elaborate air cleaning apparatus or to an external flue or chimney or the like.

In use, the fans 40 may be operated continuously or may be energized by closure of a power supply switch (not shown) operated automatically by opening of the lid 32, so that air is sucked through the gaps or vents 36 when the lid is opened.

As illustrated, the major part of the panel 10, with the deck and the reaction vessel 26 may be formed as an integral plastics moulding, the fans 40 being fitted after moulding and the manifolds 38 being closed by respective elongate closure plates subsequently secured in place, for example by screws.

In the present specification "comprise" means "includes or consists of" and "comprising" means "including or consisting of".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

What is claimed is:

1. A laboratory apparatus, comprising a container for containing material which may emit noxious fumes, the container having a closure moveable between an open position and a closed position in which it closes off or opens a mouth of the container and wherein a fume collecting arrangement is provided comprising vents provided adjacent said mouth of the container and means operable to draw in air through the vents, with fumes escaping from the container, whilst the closure is in said open position, and to pass the air carrying said fumes to treatment means or to a disposal outlet.

2. An apparatus according to claim 1, wherein said means operable to draw in air is electrically operated and is controlled by a switch operated automatically by opening and closing said closure.

3. An apparatus according to claim 1, wherein said mouth is generally planar and said vents are in the form of elongate slots extending adjacent the said mouth and in substantially the same plane as said mouth or spaced slightly from such plane.

4. An apparatus according to claim 1 in which the container is in the form of a vessel having a mouth and top, the vessel being suitable for containing a processing fluid, and wherein said closure is a lid moveable between a lowered position closing off said mouth and a raised position in which it is clear of said mouth, to allow access to the interior of the container.

5. An apparatus according to claim 4, wherein said vents extend in a plane generally parallel with but slightly above that of said mouth.

6. An apparatus according to claim 5, wherein the vessel is incorporated in a housing providing an upwardly facing surface with an opening therein coincident with or registering with said mouth of the vessel and said lid is mounted on hinges fixed with respect to said housing for pivotal movement between said open and closed positions, the lid extending across said opening and over at least the parts of said surface surrounding said opening, and wherein said vents are arranged adjacent respective ones of two opposite edges of the lid.

7. A device according to claim 6, wherein said lid, in its closed position, is located in a recess, the bottom of which provides said surface, said opposing edges of the lid, in the closed position of the latter, lying adjacent respective edges of said recess to define respective gaps and wherein said vents are arranged in the region of said gaps.

* * * * *